United States Patent [19]
Mitter et al.

[11] Patent Number: 5,348,761
[45] Date of Patent: Sep. 20, 1994

[54] USE OF A SWELLABLE PLASTIC AND PROCESS FOR MAKING A RESISTIVE MOISTURE SENSOR

[75] Inventors: Helmut Mitter, Hellmansödt; Walter Scharizer, Gallneukirchen, both of Austria; Herbert Söllradl, Emmerting, Fed. Rep. of Germany; Norbert Rossak, Neukirchen a.d. Vöckla, Austria

[73] Assignees: E + E Elektronik Gesellschaft m.b.H., Langwiesen; Lenzing Aktiengesellschaft, Werkstrasse, both of Austria

[21] Appl. No.: 835,471
[22] PCT Filed: Aug. 29, 1990
[86] PCT No.: PCT/AT90/00084
  § 371 Date: Feb. 28, 1992
  § 102(e) Date: Feb. 28, 1992
[87] PCT Pub. No.: WO91/03734
  PCT Pub. Date: Mar. 21, 1991

[30] Foreign Application Priority Data
Aug. 29, 1989 [AT] Austria .......................... 2033/89
Mar. 9, 1990 [AT] Austria ............................ 571/90

[51] Int. Cl.$^5$ ............................................ B05D 5/12
[52] U.S. Cl. ................................. 427/101; 324/694; 338/35; 252/408.1; 252/963; 252/511; 252/512; 524/424; 524/439; 524/495; 524/496

[58] Field of Search ................. 324/694; 427/8, 101; 338/35; 524/424, 439, 495, 496; 252/408.1, 963, 511, 512

[56] References Cited
U.S. PATENT DOCUMENTS

| | | | |
|---|---|---|---|
| 3,582,728 | 6/1971 | Thoma | 317/246 |
| 3,848,218 | 11/1974 | Wakabayashi | 338/35 |
| 3,983,527 | 9/1976 | Ohsato et al. | 338/35 |
| 4,473,813 | 9/1984 | Kinjo et al. | 338/35 |
| 4,635,027 | 1/1987 | Miyoshi et al. | 338/35 |
| 4,761,710 | 8/1988 | Chen | 361/286 |
| 4,965,698 | 10/1990 | Thoma et al. | 361/286 |
| 5,001,453 | 3/1991 | Ikejiri et al. | 338/35 |
| 5,050,434 | 9/1991 | Demisch | 73/336.5 |

FOREIGN PATENT DOCUMENTS

| | | | |
|---|---|---|---|
| 234789 | 3/1974 | Fed. Rep. of Germany . | |
| 63-127150 | 5/1988 | Japan | 338/35 |
| 1464605 | 2/1977 | United Kingdom . | |
| 2222261 | 2/1990 | United Kingdom | 324/694 |

Primary Examiner—Terry J. Owens
Assistant Examiner—Erma Cameron
Attorney, Agent, or Firm—Cushman, Darby & Cushman

[57] ABSTRACT

A process is disclosed for producing a swellable plastic resistive moisture sensor comprising dispersing an additive selected from the group consisting of carbon in powder, dust or soot form, carbon black, graphite, a metal in powder or dust form, and mixtures thereof, into a plastic comprising a polyimide or a copolyimide or both formed from diisocyanate and dianhydride reactants.

10 Claims, 1 Drawing Sheet

USE OF A SWELLABLE PLASTIC AND PROCESS FOR MAKING A RESISTIVE MOISTURE SENSOR

BACKGROUND OF THE INVENTION

The invention relates to the use of a swellable plastic, which additives, such as carbon, for example carbon black, metal dust or the like, are dispersed for improving conductivity, for producing a resistive moisture sensor, as well as a method for producing such a resistive moisture sensor.

Resistive moisture sensors, i.e. moisture sensors which change an electrical resistance as a function of humidity, having metal or semiconductor oxides as moisture-sensitive material are known. The said moisture-sensitive materials are mainly used in the form of sinter bodies, ceramic materials, foils, fired thick film pastes and chemically deposited coatings. Moisture sensors of this type are distinguished in the said embodiments by high sensitivity, i.e. large resistance changes with changes of the humidity, but are stable to only a small extent and have relatively sluggish response properties and particularly long response times. Because the moisture-retaining volume of such sensors is comparatively large, the sluggish response characteristics are understandable.

In addition, metal or semiconductor oxide moisture sensors generally have a strong non-linear resistance-moisture characteristic as well as relatively large resistance, which increases the expenditures in connection with the evaluation electronics. Sensors of the above mentioned types can be found, for example, in German Letters Patent 16 98 096, German Published, Non-Examined Patent Applications DE-OS 27 28 092 and DE-OS 30 24 297, in U.S. Pat. No. 3,453,143 and German Published, Examined Patent Application DE-AS 29 38 434.

SUMMARY OF THE INVENTION

It is the object of the invention to make a resistive moisture sensor available which can be produced in a simple manner and which is distinguished by satisfactory linearity of the resistance-moisture characteristic and by a resistance level particularly suited for evaluation. In accordance with the invention it is proposed in this connection to use a swellable plastic and in which additives, such as carbon, metal dust or the like have been dispersed for improving the conductivity, for producing a resistive moisture sensor. Swellable plastics, such as polyimides, have already been proposed in connection with capacitive moisture sensors. But that swellable plastics with appropriate additives for increasing conductivity are suitable for producing resistive moisture sensors has not been suggested in any manner. The mechanism for the function of such a swellable plastic as a matrix for additives which increase conductivity for producing a resistive moisture sensor has by no means been completely clarified. The resistance-moisture characteristic, surprisingly shown to be relatively linear, is put down to an increase in the relative distance of the additives, which increases conductivity caused by swelling of the swellable plastic because of increasing moisture, so that a positive change in resistance is observed with increasing moisture. In this connection the use of a polymer matrix made of a swellable plastic has the advantage that it is possible to operate with relatively thin layers, because of which the response speed can be considerably increased, while the fact that the basic conductivity is attained by additives, such as carbon, for example carbon black, metal dust or the like, offers the chance of producing resistive moisture sensors with advantageous resistance values evaluation electronics connected downstream, while the resistance value can be set over a wide range. Besides the essentially linear positive resistance characteristics, the high response speed is surprising, which is accompanied by a definite improvement along with particularly simple production of the moisture sensor. Polyimides, copolyimides, aramides, polyamides, polyacrylates, poly-methacrylates, polycarbonates, polysulfones or polyethylene are advantageously used as swellable plastics for the production of such resistive moisture sensors, where in a preferred manner up to 50 weight-% of graphite or 3 to 15 weight-% of carbon black with a specific surface of more than 100 $m^2/g$, in particular 1000 $m^2/g$, are used as conductivity additives. A high degree of stability and high linearity of the resistance-moisture characteristic can be achieved in that the conductivity additives are introduced with dispersion agents, such as siloxanes, and have a maximum particle size of 25 $\mu m$.

DESCRIPTION OF THE PREFERRED EMBODIMENTS

Figure 1:
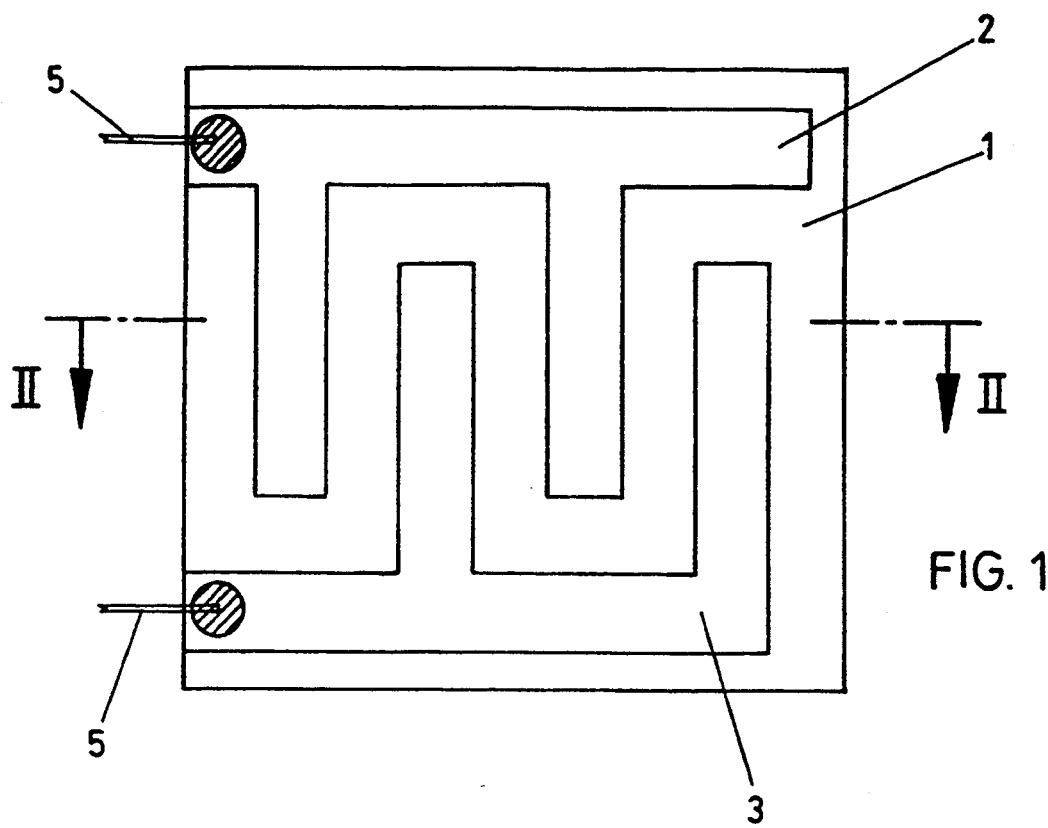
FIG. 1 is a top plan view of a moisture sensor according to the present invention.

It is possible in principle to apply such a swellable plastic in the conventional manner to an appropriate insulating support material to assure mechanical stability. After the addition of conductivity additives, the sensor material can be applied by spinning, dipping or spraying, or even by painting, pressing or the like where, in particular in case of the preferred use of polyimides as the swellable plastic, a particularly advantageous process for making such a resistive moisture sensor essentially consists in dissolving swellable plastics, in particular polyimides and/or copolyimides, in a polar solvent, such as N-methylpyrrolidone, then dispersing and homogeneously distributing conductivity additives, such as carbon black, in the solution and subsequently applying the solution to an inert support and then drying it. Already completely imidized materials can be used for dissolving polyimides and/or copolyimides in polar solvents, because of which it is possible to achieve particularly homogeneous and correspondingly thin layers with correspondingly great response speeds. The use of polar solvents which can be removed by drying permits in a simple manner the application of homogeneous and thin layers of swellable plastics and containing the previously introduced additives which increase conductivity on a mechanically stable inert support. It is possible to use in a conventional manner glass, ceramic materials, oxidized silicon wafers or the like as insulating support materials, where the use of polyimides in a completely imidized state in a polar solvent makes it possible to attain arbitrary layer thicknesses of complete homogeneity, because no chemical reaction takes place in the coating during the subsequent removal, particularly evaporation, of the solvent and in this way the danger of the formation of inhomogeneities on the surface is avoided. In this way it is possible to set reproducible resistance values even with small layer thicknesses. In accordance with the invention, drying is preferably performed in such a way that drying is performed in at least two stages, where drying takes place in the first stage at temperatures between 80° and 140° C., in particular 120° C., and in each succeeding stage drying takes place at a temperature increased by 50° to 80° C., because of which a homogeneous and smooth surface is attained, which makes it possible to achieve reproducible response properties with essentially the same basic setting of the resistance value. In the case of resistive moisture sensors, the cover electrode permeable to moisture required for capacitive moisture sensors is omitted, so that comparatively short response times become possible. In the case of polyimides, dimethyl formamide, dimethyl acetamide, dimethyl sulfoxide, N-methylpyrrolidone or sulfolane can be used as polar solvents, where complete dissolving in such a polar solvent can be assured if a copolymer of 3,3', 4,4'-benzophenone tetra carboxylic acid dianhydride and 60 to 100 mol-% of toluylene diamine (2, 4- and/or 2,6-isomers) or toluylene diisocyanate (2, 4- and/or 2,6-isomers) and 0 to 40 mol-% of 4,4-methylene-bis-(phenylamine) or 4,4'-methylene-bis-(phenylisocyanate) and in particular a linear polyimide with a mean weight of 30000 to 300000 units and a mean number of 10000 to 60000 is used as polyimide. A linear polyimide of this type can be applied from the solution by dipping, spraying or spinning, and in this way it is assured that the applied layer is of even thickness and free of pinholes over the entire surface, where it is possible to apply the layers with considerably reduced thickness, which is of special importance particularly in regard to response speed.

A copolymer of 3,3',4,4'-benzophenone tetra carboxylic acid dianhydride and 60 to 100 mol-% of toluylene diamine (2, 4- and/or 2,6-isomers) or toluylene diisocyanate (2, 4- and/or 2,6-isomers) and 0 to 40 mol-% of 4,4'-methylene-bis-(phenylamine) or 4,4'-methylene-bis-(phenylisocyanate) was found to be a linear polyimide with particularly high sensitivity and with improved response properties in comparison with conventional polyimide foils. Use of such a copolymer, in particular such a copolymer with a mean weight of 30000 to 300000 units and a mean number of 10000 to 60000 is distinguished by being readily soluble in the above mentioned strong polar solvents, where the adhesion and particularly the danger of slipping or separation of the polyimide layer formed after drying can be assuredly prevented in that, prior to the application of the polyimide coating, a coupling agent, in particular carbonfunctional silanes with one or several functional terminal groups (such as aminopropyltriethoxysilane, aminoethylaminopropyltrimethoxysilane, or 3-glycidoxypropyltriethoxysilane, etc.) is applied. Carbon-functional silanes of this type are easy to process and exhibit great affinity to the conventionally used support materials, such as glass, ceramic material, metal or the like as well as to the linear soluble polyimides use for producing the moisture-sensitive layer. Because of the ready solubility of such carbon-functional silanes not only in aqueous but also non-aqueous solvents, it is possible to apply extremely thin layers of the coupling agent on the support material by dipping, spraying or spinning, in particular, so that the total thickness of the sensor is only insignificantly increased by the coupling agent.

Complete removal of the polar solvents in several stages in the cited temperature ranges results in a thin homogeneous polyimide layer on the support and even drying of the polyimide over the entire surface and depth of the component. At the same time and surprisingly, further linearization of the resistance-moisture characteristic is achieved with such temperature treatment, where the maximum drying temperature is selected to be less than 280° C., preferably approximately 260° C.

To keep the effort for the evaluation circuit connected downstream small, the specific resistance of the conductive swellable plastic is preferably set to 0.5 $\Omega$cm to 50 $\Omega$cm, in particular 5 $\Omega$cm to 30 $\Omega$cm.

Following conditioning of the polymer by drying, setting or, if required, curing performed in this manner, the connection contacts previously provided on the support can be uncovered mechanically, by means of a laser or by plasma etching, and the sensor can be provided with connecting wires by bonding.

Application of the polymer matrix in this case can be made directly on the support or, if required, with the interposition of a coupling agent where, for resistive sensors the electrode structure can also be provided over the polymer by cathodic evaporation or sputtering and, if required, photo-lithographically structured. With an embodiment of this type, the polymer need no longer be removed from the connecting wires, so that structuring of the polymer can be omitted.

Figure 2:
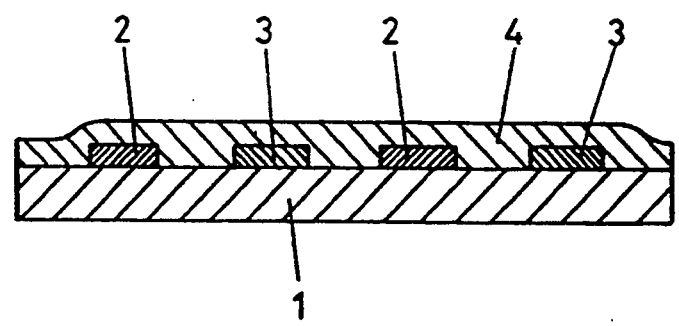
FIG. 2 is a cross-sectional view taken along line II—II in FIG. 1.
Figure 3:
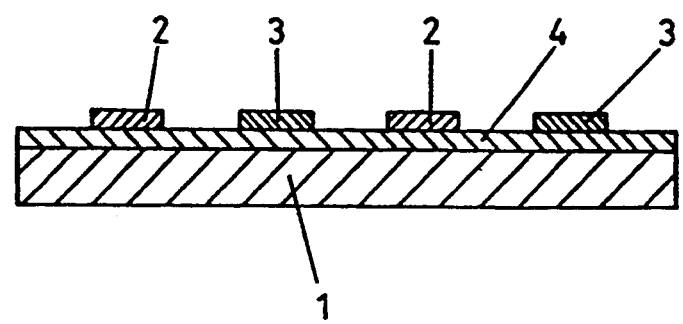
FIG. 3 is a cross-sectional view of an alternative embodiment of the present invention.

In FIGS. 1, 2 and 3 an insulating support is designated by 1, which, for example, can be made of glass, a ceramic material, in the form of an oxidized silicon wafer or other electrically insulating organic or inorganic support materials. First a layer of NiCr with a thickness of 200 nm and then a layer of Au with a thickness of 150 nm is applied on the cleaned and dried support 1 in a process by means of a cathode sputtering method. This NiCrAu layer is then photo-lithographically structured in the shape of interlocking comb electrodes 2 and 3.

A solution of a dissolved polyimide or copolyimide, which is still soluble in the fully imidized state in a polar solvent and which was made conductive by the addition of approximately 6% of carbon black in relation to the polyimide portion of the solution, is applied to the cleaned and dried surface, possibly treated with a coupling agent, of the substrate provided with electrodes 2 and 3, and is subsequently dried.

The thin polymer layer 4 is subsequently removed from atop the connecting surfaces of the electrode either mechanically or by plasma etching or by means of a laser, to allow the bonding of the electrodes 2, 3 with connecting wires 5.

A linear copolymer of 3,3',4,4'-benzophenone tetra carboxylic acid dianhydride and 60 to 100 mol-% of toluylene diamine (2, 4- and/or 2,6-isomers) or toluylene diisocyanate (2, 4- and/or 2,6- isomers) and 0 to 40 mol-% of 4,4'-methylene-bis-(phenylamine) or 4,4'-methylene-bis-(phenylisocyanate) in a strongly polar solvent such as dimethyl formamide, dimethyl sulfoxide, N-methyl pyrrolidone or sulfolane is employed for the polyimide layer 4 made conductive by the addition of carbon black or graphite. Following application of such a copolymer with a mean weight of 30000 to 300000 units and a mean number of 10000 to 60000, the polyimide was dried in stages at temperatures of above 105° C. to maximally 280° C., where drying was performed in three stages and in each of the three stages the temperature was increased by 50° C. to 80° C. over the previously prevailing temperature. For example, drying was performed at 120° C., 190° C. and 260° C. The linear polyimide was applied from the solution by dipping, spraying or spinning. In principle, processing of the linear copolyimide to make the polyimide layer 4 is possible directly from the solution obtained by polycondensation. However, the polyimide can also be precipitated, dried and stored beforehand and a suitable solution be prepared only when needed.

In the embodiment in accordance with FIG. 3 the solution of the polyimide, made conductive by carbon black or graphite, is again applied by spinning to the cleaned and dried surface of the substrate or the support 1 which, if required, was treated with a coupling agent, and dried in a circulating air furnace in three stages at approximately 120° C., 190° C. and 260° C.

First a layer of NiCr with a thickness of 200 nm and then a layer of Au with a thickness of 150 nm is applied on the conductive polyimide layer 4 made in this way in a process by means of a cathode sputtering method. This NiCr-Au layer is then also photo-electrically structured in the shape of interlocking comb electrodes 2 and 3 and provided with connecting wires.

Particularly small layer thicknesses and thus high response speeds can be obtained by spinning and pressing, where a range of thickness of 0.3 $\mu$m to 10 $\mu$m, preferably 0.5 $\mu$m to 2 $\mu$m, is considered.

We claim:

1. A process for producing a swellable plastic resistive moisture sensor comprising dispersing an additive selected from the group consisting of carbon in a powder, dust or soot physical state, carbon black, graphite, a metal in a powder or dust physical state, and mixtures thereof, into a plastic comprising a polyimide or a copolyimide or both formed from diisocyanate and dianhydride reactants.

2. The process according to claim 1, wherein said additive is selected from the group consisting of graphite in a weight percent concentration of up to 50% and carbon black in a weight percent concentration of 3–15%, wherein said additive has a specific surface area of 100 m/g to 1000 m/g.

3. The process according to claim 1, wherein dispersing agents are used for said additive and said additive has an average particle size of 25 micrometers or smaller.

4. The process according to claim 1, further comprising dissolving a polyimide or a copolyimide, having been completely imidized, in a polar solvent, dispersing said additive using a dispersing agent until the additive is homogeneously distributed in the polyimide or copolyimide, and applying said polyimide or copolyimide with said additive to an inert support, and drying.

5. The process according to claim 4, wherein drying is conducted in at least two to seven stages, with the first stage at a temperature ranging between 80° and 140° C., and each succeeding stage at a temperature increased by 50° to 80° C.

6. The process according to claim 5, wherein the maximum drying temperature for any stage is 280° C.

7. The process according to claim 5, wherein the maximum drying temperature for any stage is 260° C.

8. The process according to claims 4 or 5, wherein the specific resistance of said plastic is 0.5 to 50 kiloOhm-cm.

9. The process according to claims 4 or 5, wherein the specific resistance of said plastic is 5 to 30 kiloOhm-cm.

10. The process according to claim 4, wherein said copolyimide comprises, 3,3'4,4'-benzophenone tetracarboxylic acid dianhydride and at least one compound selected from the group consisting of toluylene diamine and toluylene diisocyante and at least one compound selected from the group consisting of 4'4-methylene-bis-(phenylamine) and 4,4'-methylene-bis-(phenylisocyanate), in a polar solvent.

* * * * *